(12) United States Patent
Hall et al.

(10) Patent No.: US 11,564,666 B2
(45) Date of Patent: *Jan. 31, 2023

(54) TOILET WITH CONSUMABLE MATERIAL SEPARATING FECES FROM BOWL

(71) Applicant: Medic, Inc., Provo, UT (US)

(72) Inventors: David R. Hall, Provo, UT (US);
Anthony E. Pullen, Tucson, AZ (US);
Jeffery Duncan, Tucson, AZ (US)

(73) Assignee: Medic, Inc., Provo, UT (US)

( * ) Notice: Subject to any disclaimer, the term of this patent is extended or adjusted under 35 U.S.C. 154(b) by 142 days.

This patent is subject to a terminal disclaimer.

(21) Appl. No.: 16/827,531

(22) Filed: Mar. 23, 2020

(65) Prior Publication Data

US 2021/0219963 A1 Jul. 22, 2021

Related U.S. Application Data

(63) Continuation-in-part of application No. 16/744,854, filed on Jan. 16, 2020.

(51) Int. Cl.
*A61B 10/00* (2006.01)
*A47K 13/24* (2006.01)
*E03D 9/00* (2006.01)

(52) U.S. Cl.
CPC .......... *A61B 10/0038* (2013.01); *A47K 13/24* (2013.01); *E03D 9/00* (2013.01)

(58) Field of Classification Search
CPC ..... A61B 10/0038; A47K 13/24; A47K 11/03
USPC ............................................ 4/484, 449, 459
See application file for complete search history.

(56) References Cited

U.S. PATENT DOCUMENTS

| | | | |
|---|---|---|---|
| 9,556,602 B2 * | 1/2017 | Claunch | ................. E03D 5/016 |
| 2004/0143893 A1 * | 7/2004 | Wu | ........................... E03D 9/10 4/319 |
| 2017/0007082 A1 * | 1/2017 | Li | .......................... A47K 11/03 |

* cited by examiner

*Primary Examiner* — Christine J Skubinna

(57) ABSTRACT

A toilet is disclosed. The toilet has a bowl adapted to receive feces, a shelf for receiving feces in the bowl, a mechanism that places a consumable material on the shelf between uses of the toilet, and a removal mechanism for removing the feces and the consumable material from the bowl. The consumable material on the shelf is to separate feces from the shelf.

20 Claims, 14 Drawing Sheets

TOILET WITH CONSUMABLE MATERIAL SEPARATING FECES FROM BOWL

CROSS-REFERENCE TO RELATED APPLICATIONS

This application is a continuation in part of application Ser. No. 16/744,854, entitled "TOILET EQUIPPED TO PROVIDE FECAL ANALYSIS" and filed on 16 Jan. 2020.

TECHNICAL FIELD

The present disclosure relates to smart toilets. More particularly, it relates to smart toilets equipped to provide health and wellness information about a user.

BACKGROUND

The ability to track an individual's health and wellness is currently limited by the lack of available data related to personal health. Many diagnostic tools are based on examination and testing of excreta, but the high cost of frequent doctor's visits and/or scans make these options available only on a very limited and infrequent basis. Thus, they may not be widely available to people interested in tracking their own personal wellbeing.

Toilets present a fertile environment for locating a variety of useful sensors to detect, analyze, and track trends for multiple health conditions. Locating sensors in such a location allows for passive observation and tracking on a regular basis of daily visits without the necessity of visiting a medical clinic for collection of samples and data. Monitoring trends over time of health conditions supports continual wellness monitoring and maintenance rather than waiting for symptoms to appear and become severe enough to motivate a person to seek care. By the time symptoms motivate seeking care, preventative care may be eliminated as an option leaving only more intrusive and potentially less effective curative treatments. An ounce of prevention is worth a pound of cure.

Just a few examples of smart toilets and other bathroom devices can be seen in the following U.S. Patents and Published Applications: U.S. Pat. No. 9,867,513, entitled "Medical Toilet With User Authentication"; U.S. Pat. No. 10,123,784, entitled "In Situ Specimen Collection Receptacle In A Toilet And Being In Communication With A Spectral Analyzer"; U.S. Pat. No. 10,273,674, entitled "Toilet Bowl For Separating Fecal Matter And Urine For Collection And Analysis"; US 2016/0000378, entitled "Human Health Property Monitoring System"; US 2018/0020984, entitled "Method Of Monitoring Health While Using A Toilet"; US 2018/0055488, entitled "Toilet Volatile Organic Compound Analysis System For Urine"; US 2018/0078191, entitled "Medical Toilet For Collecting And Analyzing Multiple Metrics"; US 2018/0140284, entitled "Medical Toilet With User Customized Health Metric Validation System"; US 2018/0165417, entitled "Bathroom Telemedicine Station." The disclosures of all these patents and applications are incorporated by reference in their entireties.

SUMMARY

In a first aspect, the disclosure provides a toilet. The toilet has a bowl adapted to receive feces, a shelf for receiving feces in the bowl, a mechanism that places a consumable material on the shelf between uses of the toilet, and a removal mechanism for removing the feces and the consumable material from the bowl. The consumable material on the shelf is to separate feces from the shelf.

In a second aspect, the disclosure provides additional details regarding what the consumable can be made from and how it could be applied.

Further aspects and embodiments are provided in the foregoing drawings, detailed description and claims.

BRIEF DESCRIPTION OF THE DRAWINGS

The following drawings are provided to illustrate certain embodiments described herein. The drawings are merely illustrative and are not intended to limit the scope of claimed inventions and are not intended to show every potential feature or embodiment of the claimed inventions. The drawings are not necessarily drawn to scale; in some instances, certain elements of the drawing may be enlarged with respect to other elements of the drawing for purposes of illustration.

DETAILED DESCRIPTION

Figure 1:
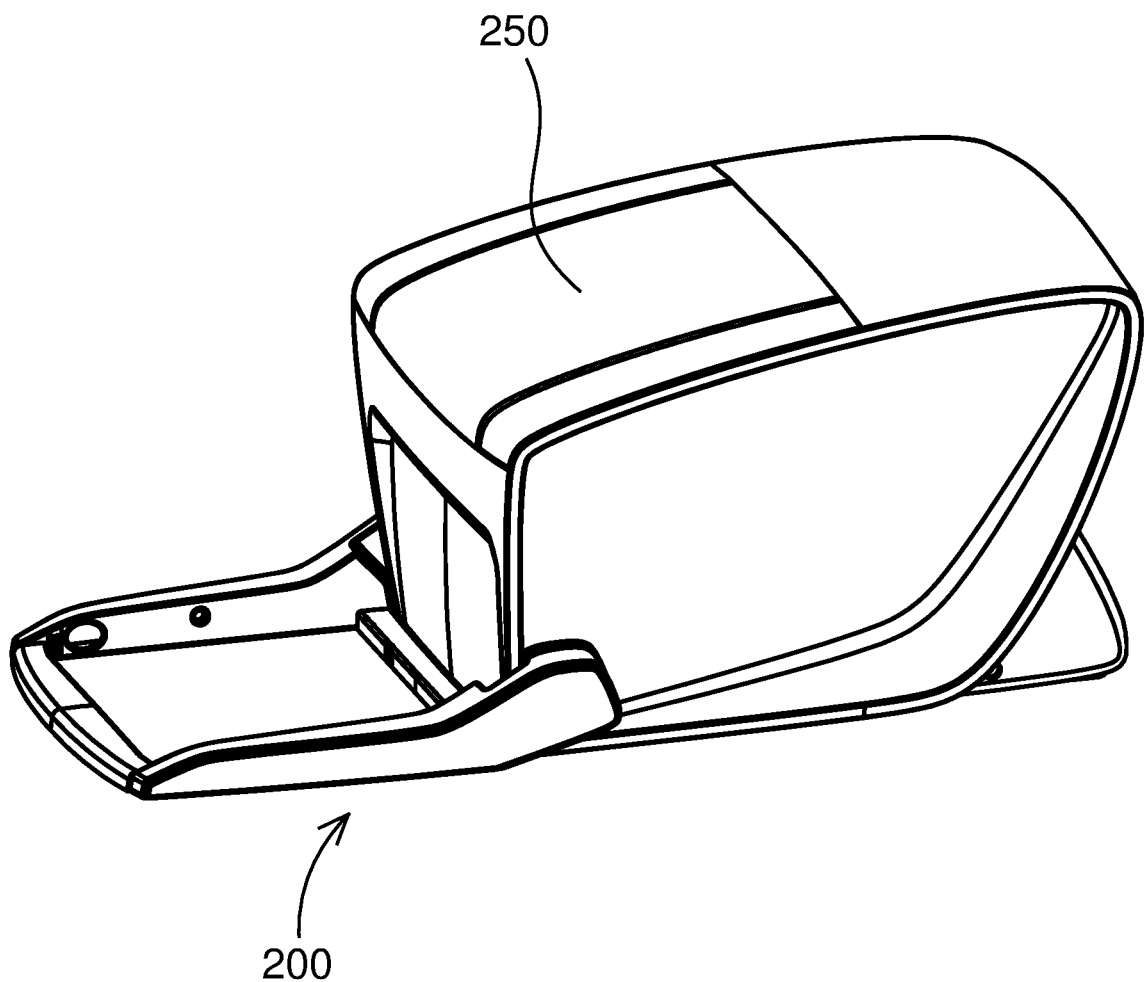
FIG. 1 is an isometric view of an exemplary embodiment of a toilet according to the present disclosure.

The following description recites various aspects and embodiments of the inventions disclosed herein. No particular embodiment is intended to define the scope of the inventions. Rather, the embodiments provide non-limiting examples of various compositions, and methods that are included within the scope of the claimed inventions. The description is to be read from the perspective of one of ordinary skill in the art. Therefore, information that is well known to the ordinarily skilled artisan is not necessarily included.

Definitions

The following terms and phrases have the meanings indicated below, unless otherwise provided herein. This disclosure may employ other terms and phrases not expressly defined herein. Such other terms and phrases shall have the meanings that they would possess within the context of this disclosure to those of ordinary skill in the art. In some instances, a term or phrase may be defined in the singular or plural. In such instances, it is understood that any term in the singular may include its plural counterpart and vice versa, unless expressly indicated to the contrary.

As used herein, the singular forms "a," "an," and "the" include plural referents unless the context clearly dictates otherwise. For example, reference to "a substituent" encompasses a single substituent as well as two or more substituents, and the like.

As used herein, "for example," "for instance," "such as," or "including" are meant to introduce examples that further clarify more general subject matter. Unless otherwise expressly indicated, such examples are provided only as an aid for understanding embodiments illustrated in the present disclosure and are not meant to be limiting in any fashion. Nor do these phrases indicate any kind of preference for the disclosed embodiment.

As used herein, "excreta" is meant to refer to human waste discharged from the body, especially in the form of feces and/or urine.

As used herein, "toilet" is meant to refer to any device or system for receiving human excreta, including urinals.

As used herein, the term "bowl" refers to the portion of a toilet that is designed to receive excreta.

As used herein, the term "base" refers to the portion of the toilet below and around the bowl supporting it.

As used herein, the term "user" refers to any individual who comes into contact with the toilet, including one who deposits excreta therein.

As used herein, the term "gas" refers to gas and vapors, particulate matter, and any other molecule that may be suspended in and flow with gas.

As used herein, the term "sensor" refers to anything that can detect properties in a quantitative or qualitative analysis, such as a sensor or transduce.

Exemplary Embodiments

The present disclosure relates to a toilet configured to receive excreta and detect at least one property of feces before disposing of the excreta. Preferably, this property is one which may be indicative of a user's health, especially when the reviewer is informed in health and wellness, such as a medical professional, specialist, or care giver.

In one preferred embodiment, a shelf in the toilet bowl receives the feces. While on the shelf, analysis of the feces is performed. Many forms of analysis are possible, some of which include weighing it, spectral analysis, high temperature processes such as burning with a laser, and capturing and analyzing the vapors. Once analysis of the feces on the shelf is complete, water may wash across the shelf and carry the feces to a secondary processing area. Once at the secondary processing area, a probe may be used to further process or analyze the feces, samples of the feces may be taken, the feces may be mixed with water to form a solution, one or more reagents may be added, and/or additional processing or analysis can be conducted. Finally, when the feces is no longer needed, a valve in the secondary processing area opens and the feces is flushed out of the toilet. Alternatively, analysis initiated while the feces is on either of the shelf or the secondary processing area may be sufficient and preclude the necessity of processing and/or analyzing at both the shelf and a secondary processing area.

Flushing the feces from the toilet as described above is one of many methods for disposing of excreta or human waste, some of which are mentioned below. In one preferred embodiment, the toilet disposes of the excrete into a sewer. In another embodiment, the toilet disposes of the excreta into a septic system. In an alternative embodiment, the toilet incinerates the excreta and vents the gases and vapors. In another embodiment, the excreta is dehydrated or turned into ash, following which it can be stored and collected later. Another alternative uses a combination of disposal methods to dispose of the excreta.

Figure 2:
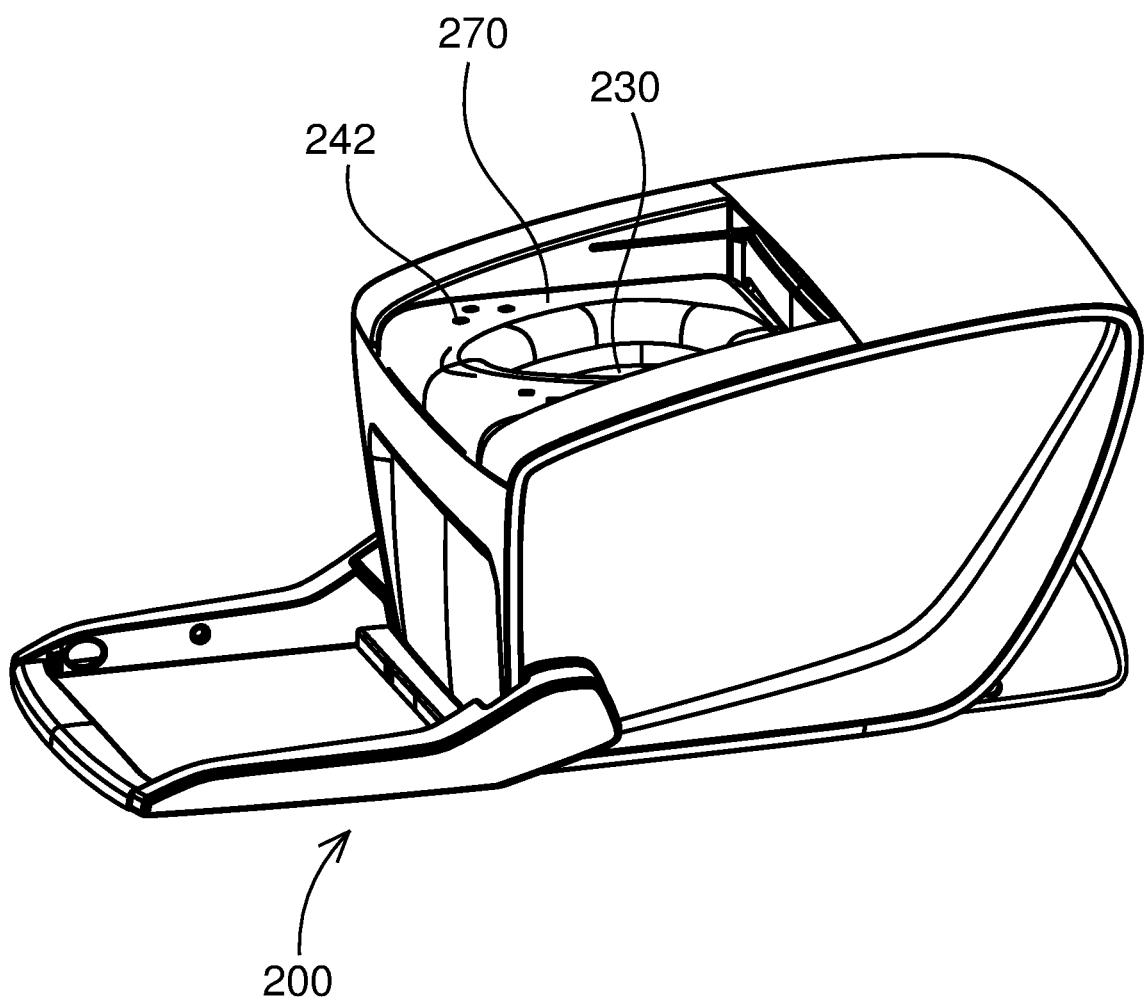
FIG. 2 is an isometric view of the toilet of FIG. 1 with the lid removed.
Figure 3:
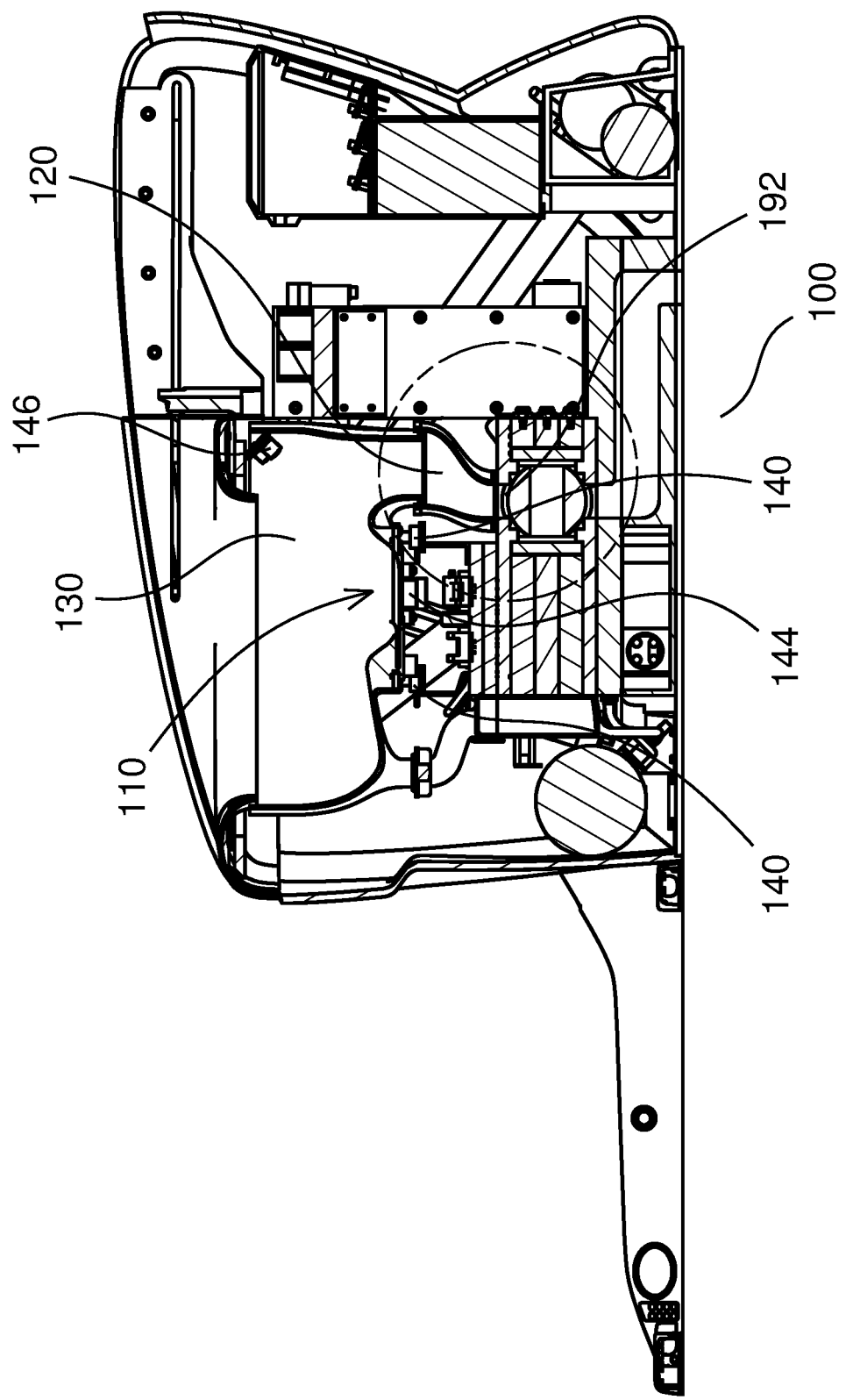
FIG. 3 is a cross section showing the inside of the toilet of FIG. 1.

FIGS. 1, 2, and 3 show embodiments of a toilet that depict a platform to receive a user's feet extending from the base. Analysis of the feet may then be conducted by sensors on or with a line of sight to the platform. The types of sensor can include any of those discussed above. More preferably, the sensors are imaging sensors and weight sensors. Additionally, the platform is connected to a motor and can be raised or lowered.

FIGS. 1 and 2 show a preferred embodiment of toilet 200. In FIG. 1, lid 250 has been closed and cooperates with other components of the toilet to form an air seal within toilet 200, enclosing the space within toilet bowl 230, especially the parts adapted to receive feces or urine, from the environment around the toilet to facilitate conducting analysis of the excreta. FIG. 2 shows the toilet 200 with the lid removed, allowing view of bowl 230 and PPG sensor 242 on seat 270. FIG. 1 shows toilet 200 with lid 250 closed. Unlike traditional toilets, this preferred embodiment may seal the toilet, excreta processing areas, and/or excreta analysis areas from the outside environment. In one preferred embodiment, there may be a seal between lid and the toilet such that there is no air gap. To ensure a sufficient seal, a seal or gasket may be placed between lid 250 and the portions of toilet 200 that mate to the lid, which may include seat 270 and the upper rim of bowl 230. Preferably the lid, the bowl, the seat, and/or other components of the toilet creating the air seal comprise a heat resistant material capable of repeated exposure to high temperatures associated with analysis incorporating heat treatment of the excreta, burning feces for analysis, or cleansing excreta from the toilet. In some embodiments there is a seal or gasket placed between the toilet seat and the upper rim of the toilet bowl to facilitate the air seal. Preferably, the seal or gasket is also made from a heat resistant material.

Referring to FIG. 3, in one preferred embodiment, there is a shelf 110 upon which feces is deposited within toilet 100. This shelf may be integrated into the bowl or alternatively may be separate from the bowl. Additionally, bowl 130 is configured to separate the urine from the feces so they may be analyzed separately from each other. Alternatively, a design may be selected in which the bowl does not separate the urine from the feces. Preferably, shelf 110 is integrated into bowl 130, toilet 100 is configured with at least one sensor 140 to measure the weight of bowl 130, and the weight and/or mass of the feces is determined from the measurements of the weight of bowl 130. Preferably, sensor 140 can also measure the impact force of the feces being deposited onto shelf 110 and/or into bowl 130. Some ways of measuring of the weight of the bowl include a pressure sensor, a strain gauge, and a scale. Preferably, sensor 140 measures the weight of bowl 130. Additionally, shelf 110 is configured with an optical or spectral analysis sensor 144. Preferably, optical or spectral analysis sensor 144 is positioned below shelf 110 and shelf 110 is configured with a transparent or translucent portion through which sensor 144 analyzes the feces. It is also possible an optical or spectral analysis sensor is located to the side and/or above the shelf or at other analysis areas in the toilet. Preferably, the sensor for detecting a property of the feces is attached or connected to the toilet and/or its internal component by physically mounting and/or via an electronic data connection.

In one preferred embodiment, when feces is initially deposited into the toilet, the shelf supports non-diarrheic feces (feces that essentially comprises non-watery stools) in a manner such that the feces is not submerged. In other words, there is minimal or no standing water in contact with the portion of the shelf where feces are deposited just prior to the feces being deposited. Preferably, the initial deposit of feces is into minimal or no standing water.

In many preferred embodiments, especially in an embodiment where the weight of the bowl is being measured, care is taken to isolate electronics from liquid and other damage. Care should also be taken to ensure containment of the excreta and in preserving the sterility of the sample collecting and testing environments. In some preferred embodiments, care is taken to isolate the sewer connection to prevent gases from the sewer from entering undesirable sections of the toilet and any space in which the toilet is installed since gasses and other contaminants in sewers can compromise excreta analysis and pollute the user environment where the toilet is installed.

The shelf allows for treatment and analysis of at least a portion of the feces. Preferably, shelf 110 is flat, approximately 3" wide by 3" long. Shelf 110 has sensor 144 positioned below the shelf and the shelf has 1-2 optically transparent or translucent portions to facilitate sensor 144 detecting at least one property of the feces on the shelf. Alternatively, the shelf is partially flat or slightly tipped from horizontal. Alternatively, the shelf is contoured and may include concave or convex portions. The shelf does not necessarily have to be separate from the bowl but can be a portion of the bowl intended to receive feces.

Moving the feces off the shelf can be done in many ways. The selection of the method and the variables inherent to each method depend on many considerations, including what processing and analysis has already been performed, what additional processing and analysis will be performed, effectiveness of moving the feces, resource requirements (e.g., power, water, time, consumables, etc.), and effectiveness of cleaning and/or sterilizing the shelf. A selection of methods is described below. Each method can be implemented independently or as a combination of multiple methods.

As mentioned above, water can wash across the shelf to carry the feces from the shelf into the secondary processing area, such as represented by secondary processing area 120 in FIG. 3. Regarding the method of using water to move the feces, there are many important variables, including water pressure, water temperature, water volume, where the water is applied, whether to purify the water, and whether to include an additive or filter. The design of the shelf will be dependent on the method selected and may dictate factors such as how the shelf is supported, the location of the shelf in the toilet, the shape of the shelf, the material or materials from which the shelf is made, and the processes used to make and install the shelf.

The water readily available will, in many cases, be tap water. The temperature of available tap water varies greatly between roughly 32° F. to 150° F. and depends on factors such as time of year, distance and method of transportation from the water supply sources or pressure boosting stations, and if the water has been heated. Generally, tap water for toilets comes from underground pipes, may be temporarily stored in a reservoir within a building, and bypasses any water heaters. Tap water pressure can vary from ambient up to 150 psi or higher. Tap water pressure depends on factors such as the pressure in the supply line or elevation of reservoirs, pressure regulators, head loss, and whether other valves in the system are open. City supplied residential water pressure is often around 40-60 psi and, when installed, pressure regulators often keep the incoming water at a maximum of 50 psi. In taller buildings, the water pressure to the building is insufficient to provide water where water is needed at sufficient pressures so pressure increasing systems may be used. Additionally, tap water has a varying molecular composition since water typically has naturally occurring trace minerals and various additives to control the quality of the water.

The characteristics of tap water supplied to the toilet may or may not be adequate. As such, the toilet may be configured to change the water in a variety of ways, including heating the water, cooling the water, purifying the water, electrolyzing the water, deionizing the water, adding additives to the water, increasing the pressure, decreasing the pressure. Additionally, such changes could be performed before the water enters the toilet.

Figure 4A:
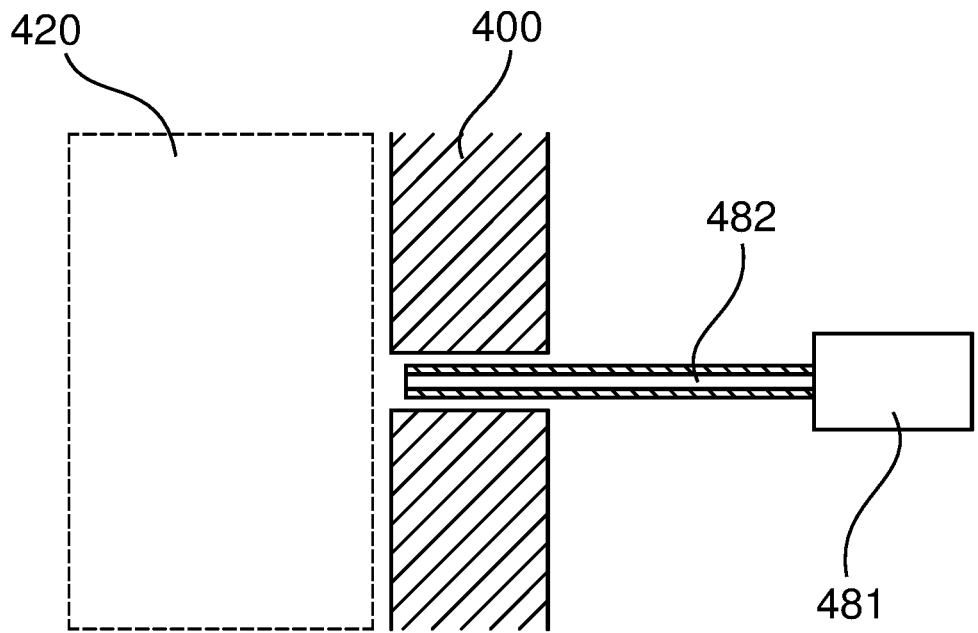
FIG. 4A is a cross section view of an exemplary embodiment of a hypodermic needle according to the present disclosure.
Figure 4B:
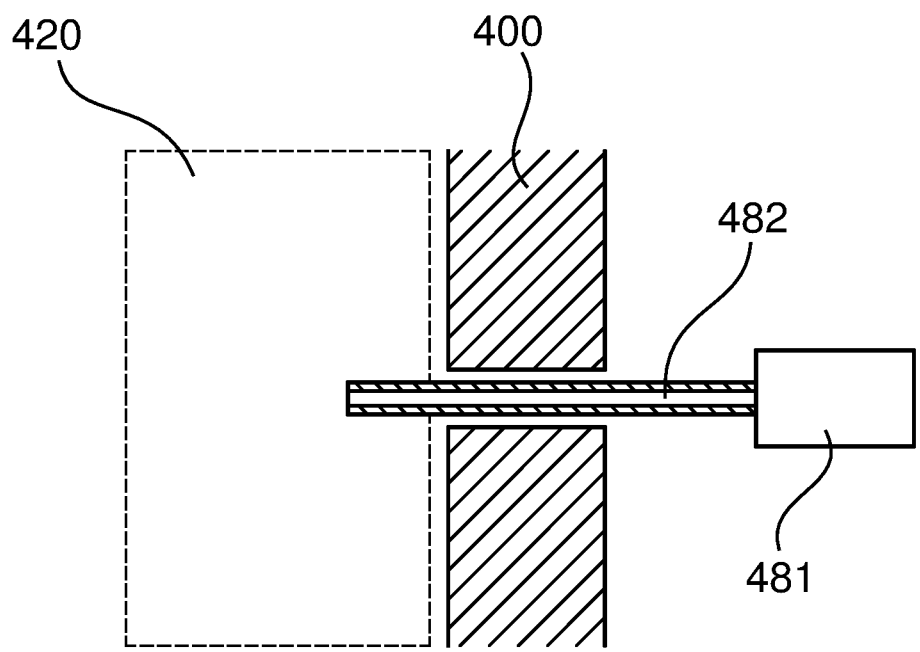
FIG. 4B is a cross section view of the hypodermic needle of FIG. 4A with one of the elements, moved to a different position.
Figure 5:
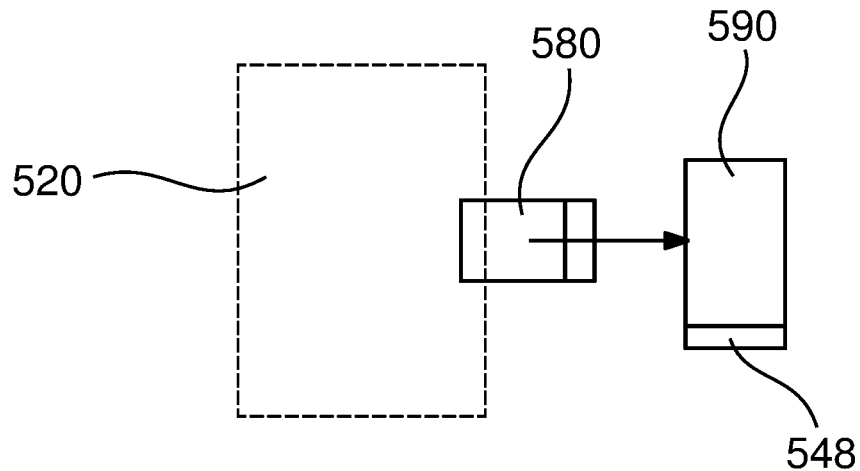
FIG. 5 is a simple diagram showing an exemplary embodiment of a probe according to the present disclosure.

Referring to FIGS. 4A, 4B, and 5, a preferred embodiment of the toilet includes a probe for collecting or analyzing a sample of the excreta.

Referring to FIG. 5, in one preferred embodiment, the toiled includes a probe 580 for collecting a sample from feces. As shown in FIGS. 4A and 4B, a probe may include a needle 482 with a hollow where the sample will be received by the needle 482 that can be driven into the feces to take the sample. In this embodiment, the probe takes a sample. In an alternative embodiment, the sample may be a surface scraping from the feces.

Accompanying a hollow needle probe may also be an ejector or ejector system 481 for removing the sample from the hollow. Preferably, the ejector system 481 is air operated with the air being injected into the needle to force the sample from the needle. The air may be produced by pumping air into the needle or by pushing a plunger into a cylinder in connection with the needle similar to a plunger in a syringe of a hypodermic needle. Alternatively, a different type of pressure differential may be created to drive the sample from the needle such as with a vacuum or pushing on the sample with a plunger. Preferably, the hollow needle probe and ejector or ejector system are configured to deposit the sample into a separate testing location, such as a reaction vessel where a reagent may be added and analysis performed.

Figure 6A:
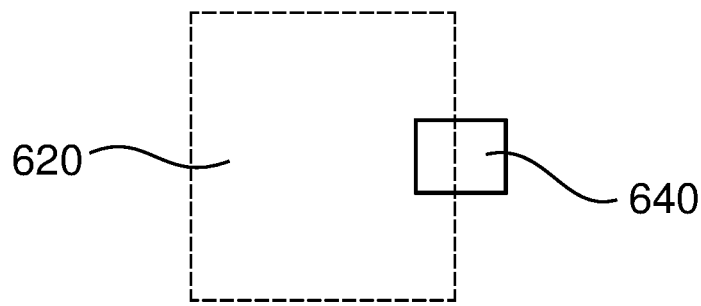
FIG. 6A is a simple diagram showing a first exemplary embodiment of a gas detector according to the present disclosure.
Figure 6B:
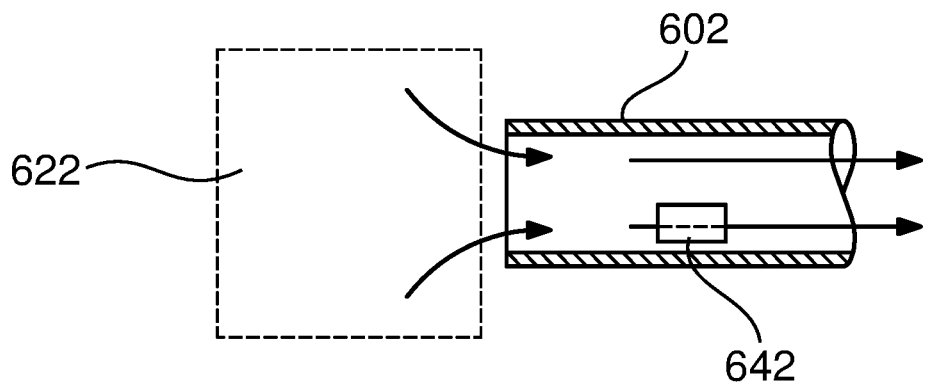
FIG. 6B is a simple diagram showing a second exemplary embodiment of a gas detector in one embodiment according to the present disclosure.

In one embodiment, a sensor detects properties of the gas in the air affected by the feces. Referring to FIG. 6A, in one embodiment, sensor 640 is in contact with an air volume 620 containing the feces and can analyze the gas in the air. In an alternative embodiment shown in FIG. 6B, a pump within the toilet may move gas from a volume of air 622 containing the feces and to a device 602 which includes sensor 642 for analyzing the gases and vapors in the air. In a preferred embodiment, the sensor can identify and measure volatile organic compounds (VOCs) and can determine what types of VOCs are being released by the fecal matter. In one embodiment, the toilet may contain a filter to purify the air and/or capture molecules in the air for analysis. Additionally, air may be actively processed or filtered to reduce the likelihood of feces odor from reaching a user while they are using the toilet.

Figure 7A:
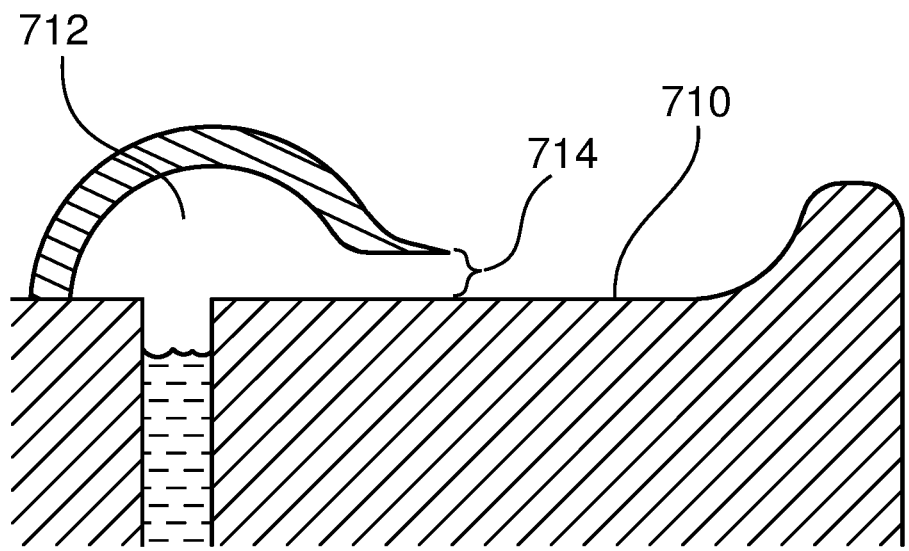
FIG. 7A is a cross section view of an exemplary embodiment of a fecal shelf according to the present disclosure.
Figure 7B:
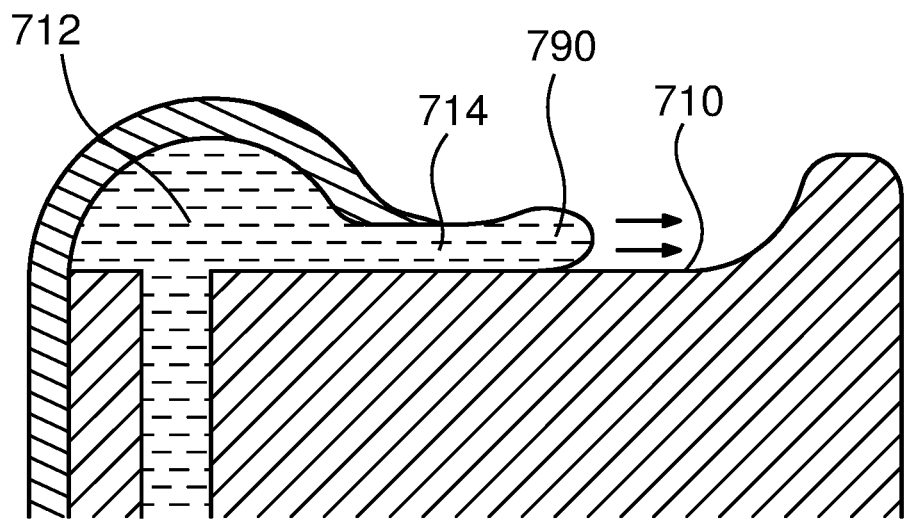
FIG. 7B is a cross section view of showing fluid being used to clean the fecal shelf of FIG. 7A.

In one preferred embodiment shown in FIGS. 7A and 7B, a volume of water may be supplied to shelf 710 via wave 790 of water. More preferably, water enters cavity 712 proximate to the shelf, wherein the cavity has an outlet 714 directing wave 790 at shelf 710 which to clean the shelf of feces. Preferably, the opening of outlet 714 is approximately ⅛"-¼" high and the width of the shelf. In one preferred embodiment, cleaning and/or sterilizing agents are added to the water to aid in cleaning and/or sterilizing the shelf.

In an alternative embodiment, there is a squeegee that wipes the shelf to remove the feces. Alternatively, one or more jet of water or a water blade is sprayed onto the shelf to remove the feces from and/or sterilize the shelf.

Figure 8A:
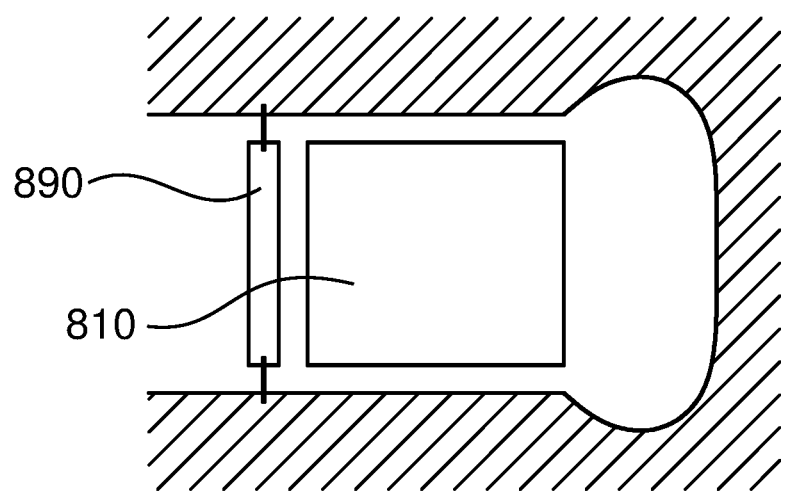
FIG. 8A is a top view of the fecal shelf in one embodiment of the invention according to the present disclosure.
Figure 8B:
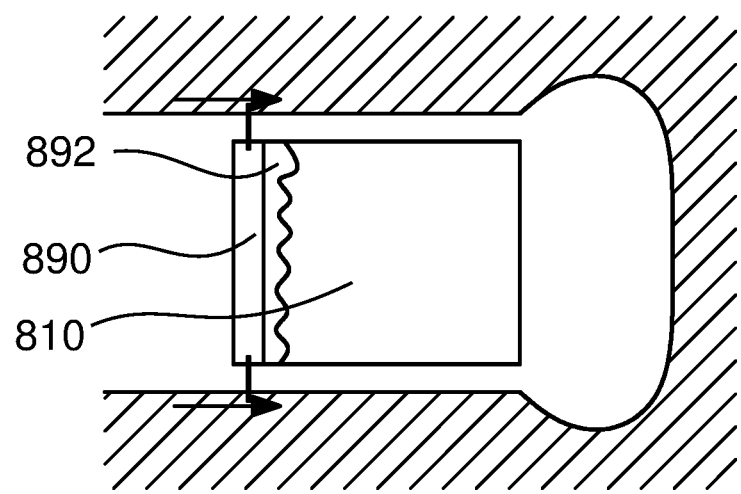
FIG. 8B is a top view of the fecal shelf of FIG. 8A with some of the movable elements moved to a second location.
Figure 8C:
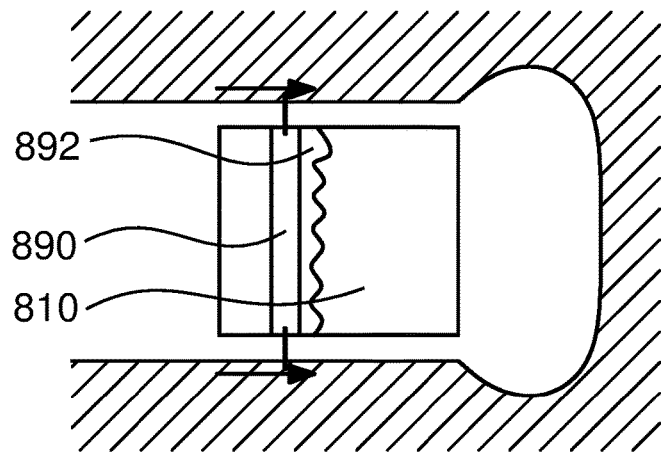
FIG. 8C is a top view of the fecal shelf of FIG. 8B with some of the movable elements moved to a third location.
Figure 8D:
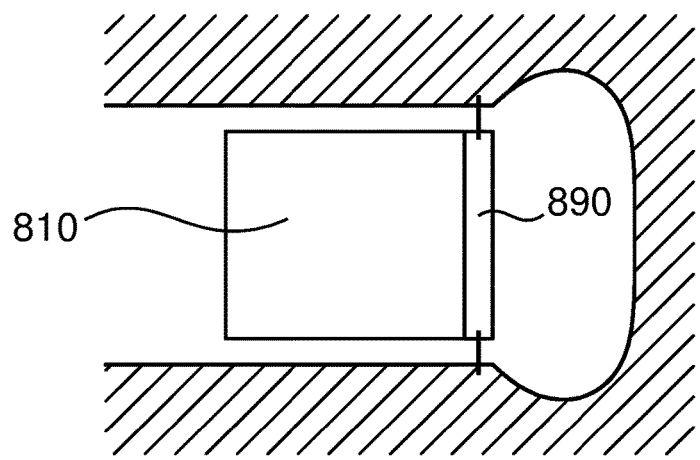
FIG. 8D is a top view of the fecal shelf of FIG. 8C with some of the movable elements moved to a fourth location.
Figure 8E:
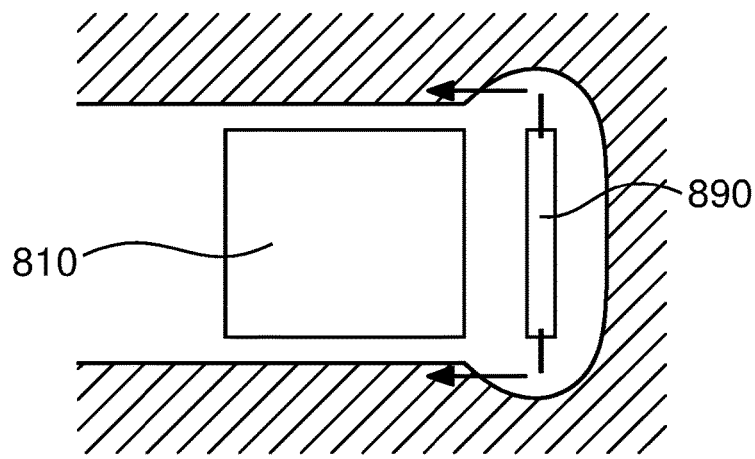
FIG. 8E is a top view of the fecal shelf of FIG. 8D with some of the movable elements moved to a fifth location.

In another embodiment depicted in FIGS. 8A, 8B, 8C, 8D, and 8E, squeegee 890 is configured so one or more water jet or a water blade sprays shelf 810 as squeegee 890 traverses shelf 810, creating water spray 892. The squeegee 890 may only travel the distance of the shelf 810 as depicted in FIGS. 8B, 8C, and 8Dd, or the squeegee 890 may also travel beyond a side of shelf 810 as depicted in FIG. 8A or 8E. Again, the water in a jet may have additives for cleaning and/or sterilizing the shelf and/or other elements of the toilet. Alternatively, the water jet or water blade of 890 and 990 could be used to apply a consumable layer on the shelf prior to feces being deposited to facilitate the removal of feces from the shelf, such as depicted in FIGS. 14A, 14B, 15A, 15B, and 15C.

Figure 9A:
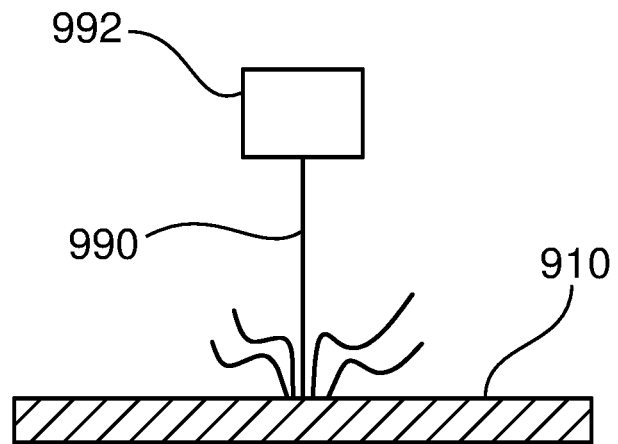
FIG. 9A is a cross section view of an exemplary embodiment of a nozzle cleaning a first part of an exemplary embodiment feces shelf according to the present disclosure.
Figure 9B:
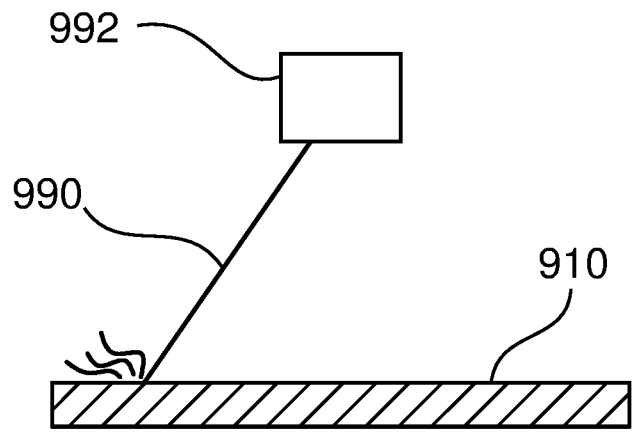
FIG. 9B is a cross section view of the nozzle and shelf of FIG. 9A with the fluid directed to a second part of the shelf.
Figure 9C:
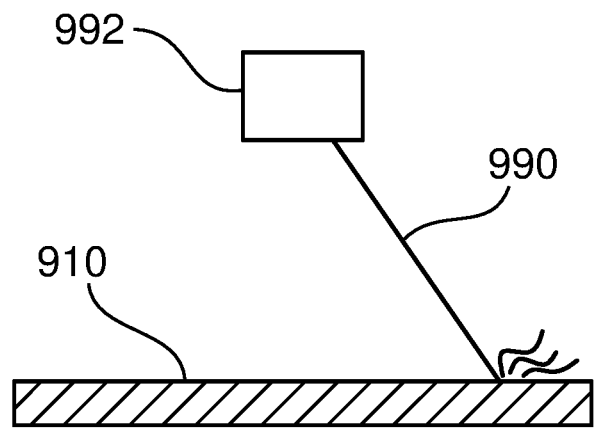
FIG. 9C is a cross section view of the nozzle and shelf of FIG. 9A with the fluid directed to a third part of the shelf.

As depicted in FIGS. 9A, 9B, and 9C, nozzle 992 supplies jet 990 and is fixed in location within the toilet. Nozzle 992 is configured to be able to change the direction of jet 990 to target specific spots on the shelf. Accompanying a directable jet would be a system for controlling the direction and a system that determines where the jet needs to be directed. The embodiment in FIGS. 8a-8e depict a system for controlling the position of the water jets. Such a system could include imaging sensors capable of detecting a stain on the shelf and/or bowl surface.

Figure 10A:
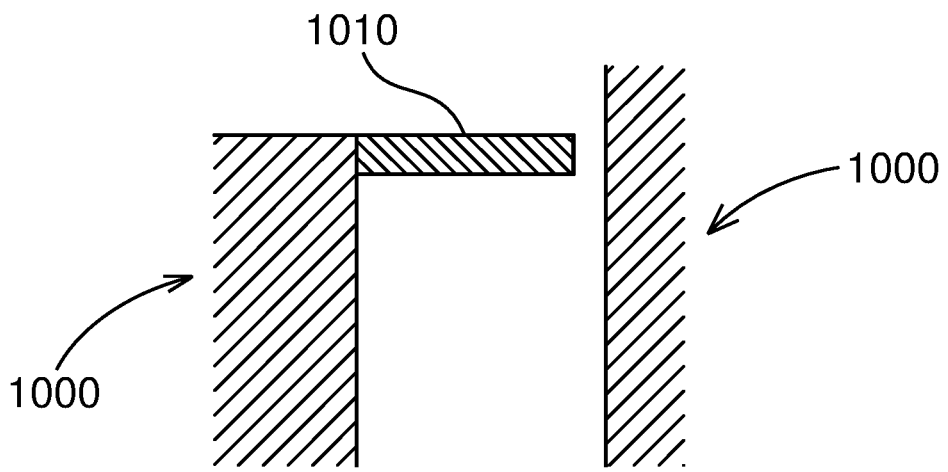
FIG. 10A is a cross section view of an exemplary embodiment of a hinged feces shelf according to the present disclosure.
Figure 10B:
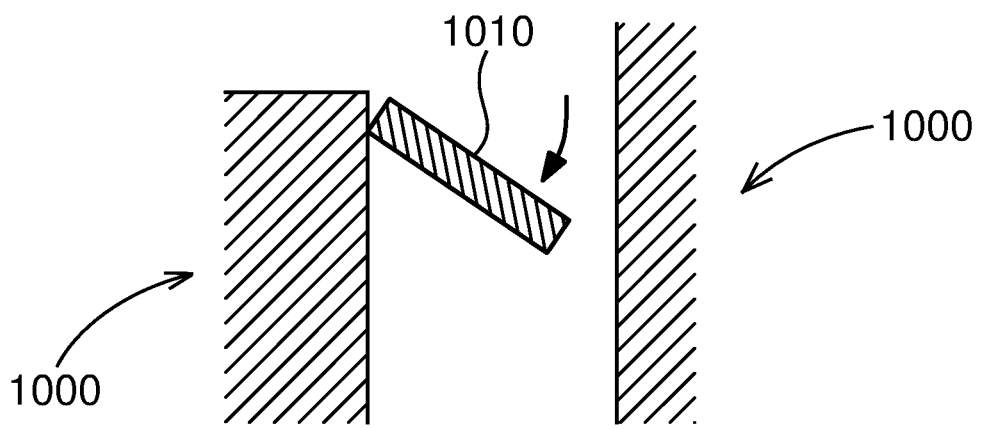
FIG. 10B is a cross section view of the feces shelf in FIG. 10A with the shelf partially lowered.
Figure 10C:
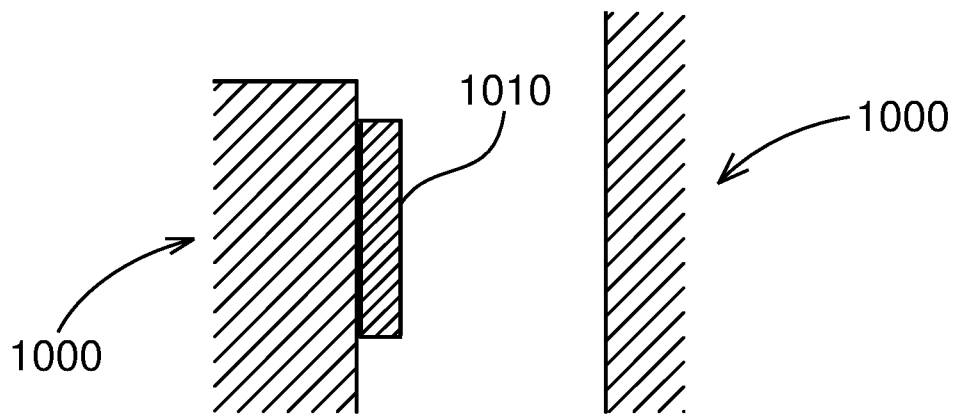
FIG. 10C is a cross section view of the feces shelf in FIG. 10A with the shelf fully lowered.

Referring to FIGS. 10A-10C, in one preferred embodiment, the shelf 1010 is cantilevered from the toilet 1000 on a hinge. Based on the analysis being performed, the shelf can be selectively released so it drops from its initial horizontal orientation to an angled or vertical orientation, at which point, the feces can slide off the cantilevered shelf and into the toilet bowl. In some embodiments, the cantilever is in connection with a pressure sensor, for example a scale or strain gauge. A measurement of the weight and/or mass of the feces may be collected prior to depositing the feces into the toilet bowl. Alternatively, the shelf may have a seam, be supported by two or more hinges, and separate relative to itself as the portions angle. FIGS. 10A, 10B, and 10C depict a cantilevered shelf. In FIG. 10A, shelf 1010 is in a horizontal or near horizontal orientation and is configured to support feces. As depicted in FIGS. 10B and 10C, when the feces is no longer needed on shelf 1010, shelf 1010 can be selectively rotated from its initial horizontal position to an angled or vertical position.

Figure 11:
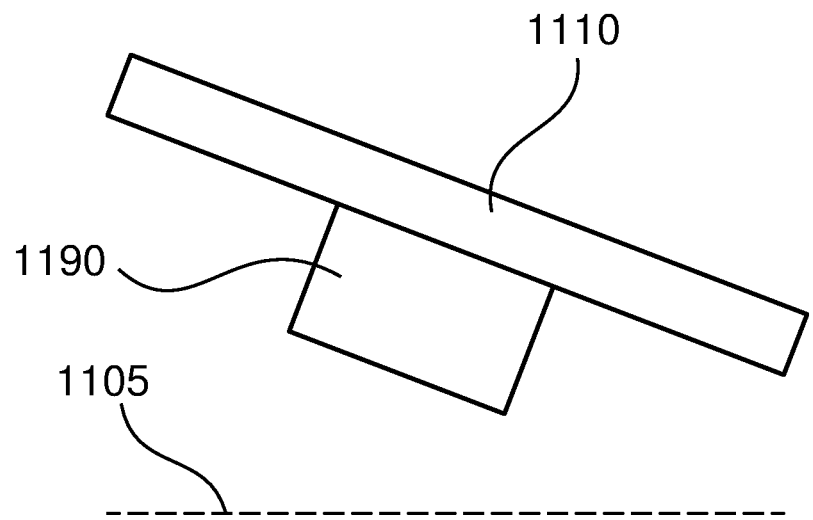
FIG. 11 is a side view of an exemplary embodiment of an angled feces shelf according to the present disclosure.
Figure 12:
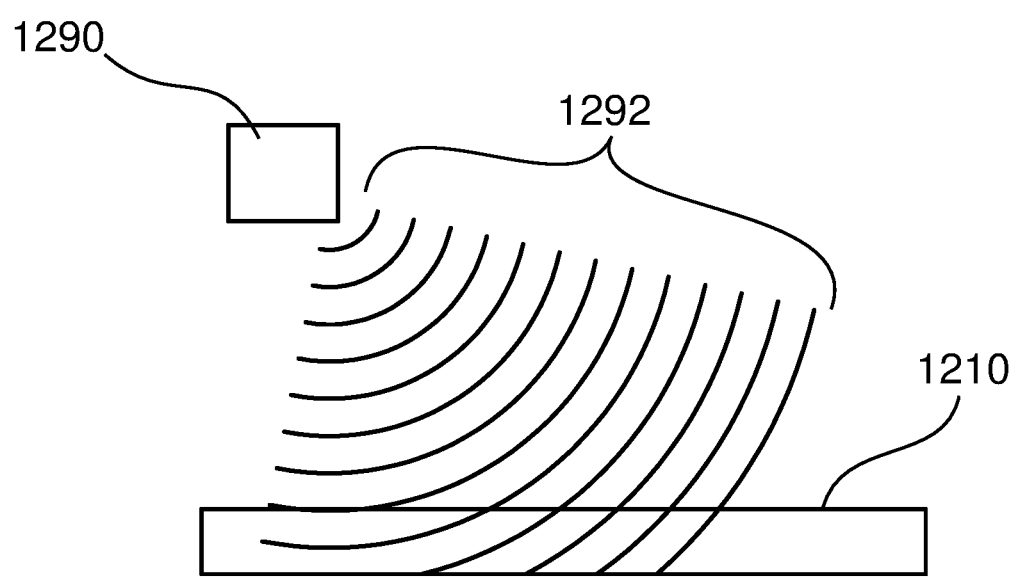
FIG. 12 is a side view of an exemplary embodiment of an acoustic cleaning of the feces shelf according to the present disclosure.

In an alternative method of moving the feces, vibration may be used to move the platform. The vibration may be applied to the feces, shelf, and/or other parts of the toilet. It may come from and in many forms, including acoustic or pressure waves, impulses, vibration motors, piezoelectric devices, or sonic or ultrasonic sources. FIG. 11 depicts one exemplary embodiment wherein shelf 1110 vibrates due to vibration source 1190 attached to shelf 1110. Preferably, shelf 1110 is at an angle offset from horizontal. Alternatively, the top of the shelf has a portion which is horizontal and another portion which is not. Alternatively, vibration of the shelf is used in conjunction with a mechanism that pushes or pulls the feces off the shelf. FIG. 12 depicts an exemplary embodiment where source 1290 is mounted with in the toilet and generates pressure waves 1292 which bombard shelf 1210. Preferably, the shelf is angled so that gravity may assist in removing the feces from the shelf. Alternatively, vibration may be used to reduce excreta to a minimum thickness for analysis.

Alternatively, a heated shelf or another source of heat (such as steam) may be applied to the bottom of the feces, a result of which might be the boiling of liquid in the feces, creating a gas layer upon which the feces can float. By floating the feces on a gas layer, the friction holding the feces in place is significantly reduced, allowing the feces to move much more freely. Once in this state, if the shelf is angled, the feces could slide off the shelf with the assistance of gravity. Also, while in this state, any portion of a force applied to the feces parallel to the shelf would have an increased effect on moving the feces. Thus, something like a small amount of air pressure or flowing water could be used to move the feces off the shelf. Possible ways of heating include microwave radiation, piezoelectric vibration, a hot plate, laser evaporation, laser ablation, mechanical mixer, and mechanical ablation.

Alternatively, a consumable material may be placed on the shelf to prevent feces from directly contacting the shelf. The selection of material and/or geometry depends on many factors, such as bowl shape, ease of technology integration, cost, governmental and other local requirements regarding waste disposal, effectiveness as preventing feces cling to the bowl, if the feces is to be used prior to disposal. This consumable material may be a pretreatment applied to the shelf, such as a hydrophobic coating, a hydrophilic coating, and/or water. It may also be a preformed solid, such as a sheet or film. As another example, it may be a powder, such as that made from talc. In one preferred embodiment, the consumable is flushed or otherwise disposed of with the feces. In such cases, the consumable is preferably biodegradable and/or otherwise in compliance to be disposed of with feces. Additionally, a portion of the feces may be used in or taken as a sample for analysis to gather health and wellness information. In these cases, the selection of the consumable should include consideration for making sure there is minimal impact on the integrity of the results from the analysis.

In one preferred embodiment, the consumable may be manually placed onto the shelf by a user or maintenance person. More preferably, the consumable is placed on the shelf automatically. For example, the consumable may come in the form of a roll of biodegradable paper which is positioned near, but materially separated from the shelf. In an automatic embodiment, a mechanism moves a portion of the roll onto the shelf, separating the portion from the roll, and ensure the material barrier is in place to prevent the roll for contact with excreta during a use of the toilet. Alternatively, rather than a roll, the consumable may be a stack of sheets. Alternatively, the sheet may be compostable or flushable rather than biodegradable. By "flushable," it is meant that whatever material is used in the consumable fits within all local and national regulations for what materials can be flushed into public sewer systems or septic systems. As another example, a hydrophobic liquid or a hydrophilic powder could be sprayed onto the shelf by a nozzle. The nozzle could be built into the toilet or into a wand. A user might manually spray it on or initiate an automatic system that sprays the consumable on prior to a use of the toilet. As yet another example, a hydrophilic gel could be spread onto the shelf by a robotic arm.

In one preferred embodiment, the consumable placed on the shelf has one or more features that can be used to pick up the consumable. For example, there could be opposing handles a person could grab. Alternatively, the features could be hooks or hook receptacles that interface with a tool or mechanism to hold consumable while it is being removed from the fecal shelf. In another preferred embodiment, measures can be taken to isolate any feces on the consumable, such as with a covering placed over the feces or a draw string which pulls the edges of the consumable together in a way that the consumable encloses the feces. Such a covering could facilitate the sanitary and/or integrity preserving removal of the feces from the toilet. This could be useful in cases where the feces may not be flushed. It could also be useful in cases where a sample of the feces needs to be removed from the toilet for analysis.

Figure 13A:
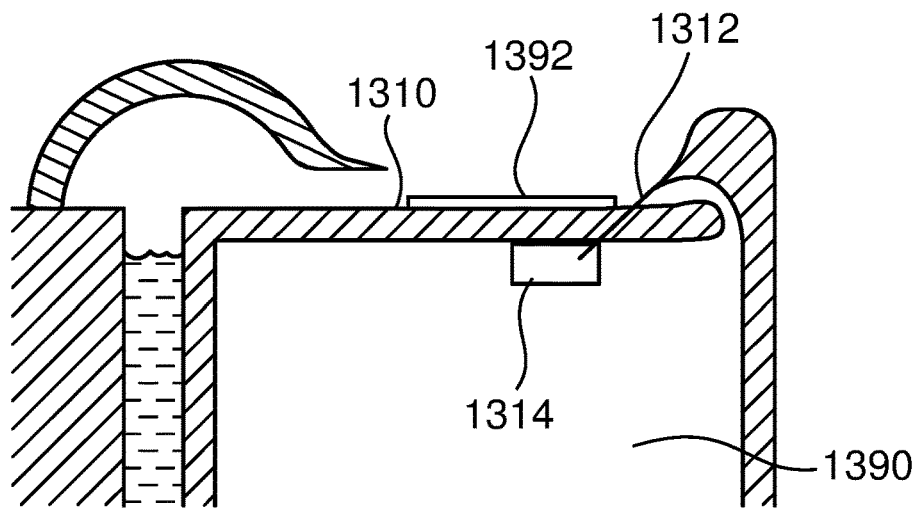
FIG. 13A is a side view of an exemplary embodiment of a consumable on the feces shelf according to the present disclosure.
Figure 13B:
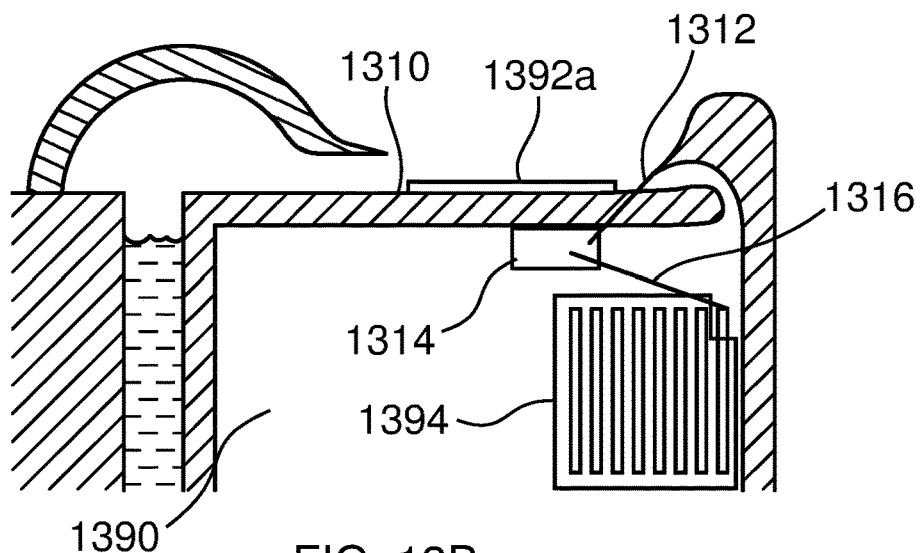
FIG. 13B is a side view of the shelf of FIG. 13A with a cartridge of consumable below the shelf.
Figure 13C:
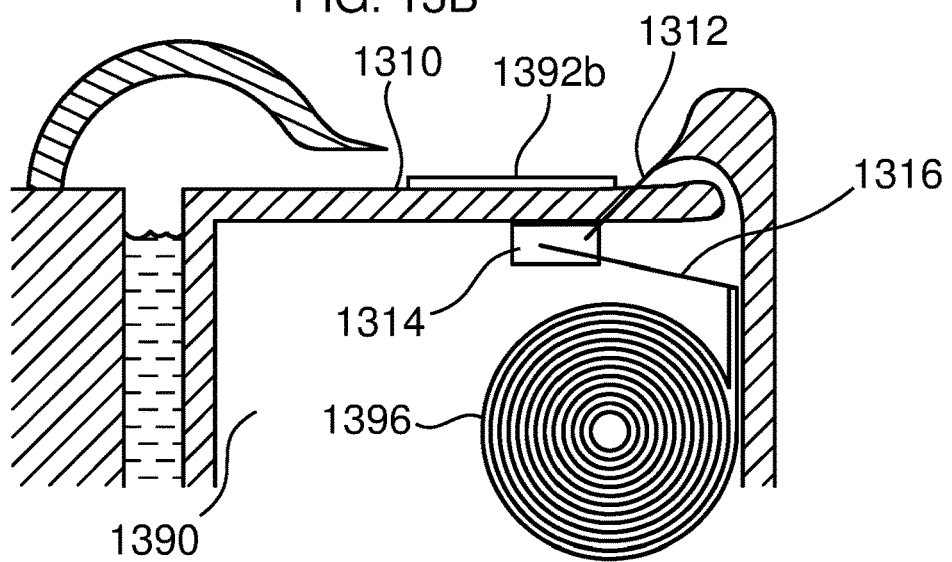
FIG. 13C is a side view of the shelf of FIG. 13A with a roll of consumable below the shelf.

Referring to FIGS. 13A, 13B, and 13C, one embodiment of the invention is shown with consumable 1392 placed on shelf 1310 prior to feces being deposited onto the shelf, consumable storage door 1312 which opens to enable access to consumable storage area 1390, and consumable mechanism 1314. In FIGS. 13B and 13C, there is an arm attached to consumable mechanism 1314 which positions consumables on feces shelf 1310. Consumable 1392 could comprise at least a be a gel or a solid material. In FIG. 13B, cartridge 1394 of consumables is stored in storage area 1390 and consumable arm 1316 places consumable 1392a onto feces shelf 1310. In FIG. 13C, roll 1396 of consumable is stored in the storage area 1390, consumable arm 1316 which moves consumable 1392a onto fecal shelf 1310, and consumable door 1312 additionally separates consumable 1392b from consumable roll 1396. Additionally, consumable mechanism 1314 may include a detector to detect whether the supply of consumable in consumable storage area 1390 is sufficient for current or near-future use.

Figure 14A:
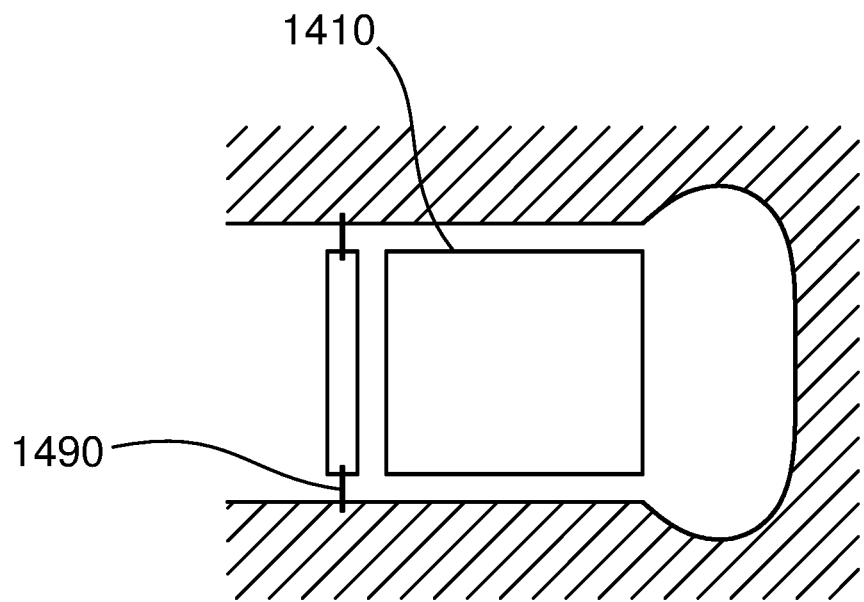
FIG. 14A is a top view of an exemplary embodiment of a consumable placer according to the present disclosure.
Figure 14B:
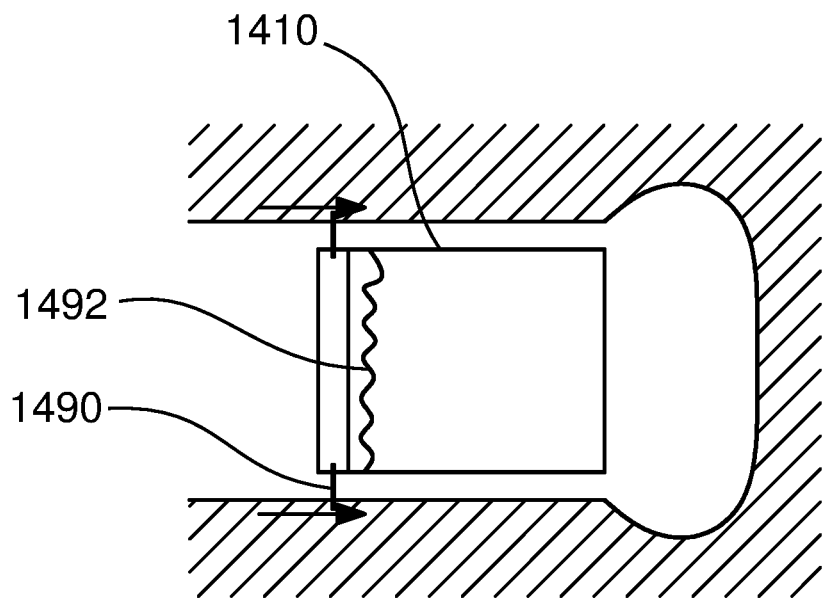
FIG. 14B is a top view of the consumable placer in FIG. 14A moved to a second location.

Referring to FIGS. 14A and 14B, one embodiment of the invention is shown with shelf 1410 and consumable depositor 1490. In FIG. 14A, consumable depositor 1490 is at rest, not placing consumable on shelf 1410. In FIG. 14B, consumable depositor 1410 is placing or spreading consumable 1492 on the shelf. Consumable 1492 could be sprayed on or spread on by consumable depositor 1490. Consumable 1492 could be a liquid, gel, or powder. Alternatively, the consumable depositor could be placing a sheet which it is pulling from another location in the toilet.

Figure 15A:
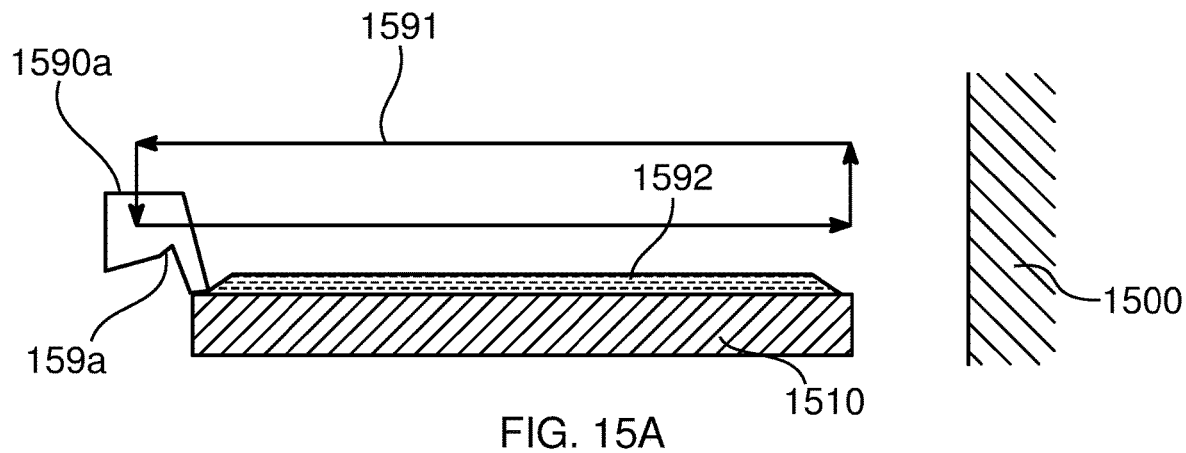
FIG. 15A is a side view of an exemplary embodiment of a liquid or gel consumable on the feces shelf according to the present disclosure.
Figure 15B:
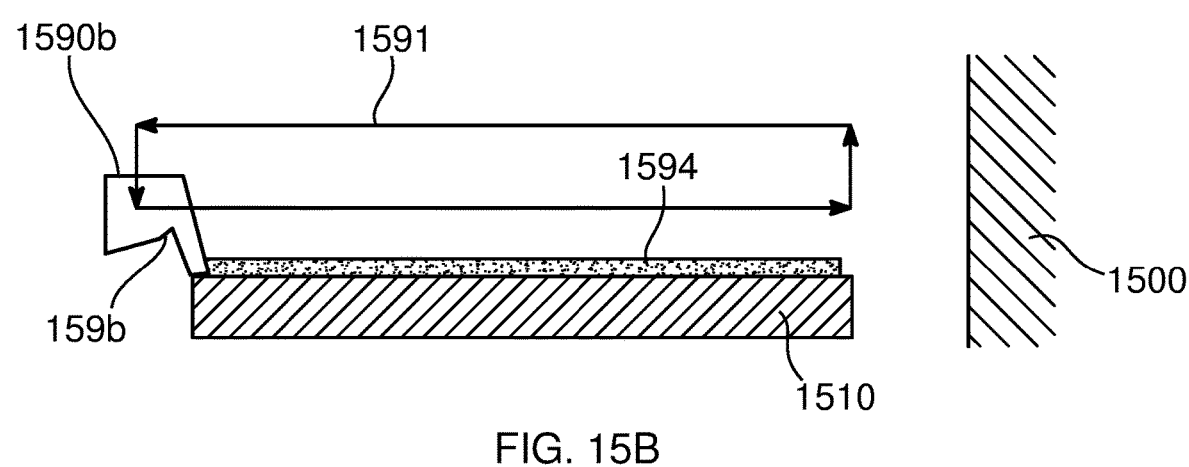
FIG. 15B is a side view of the shelf of FIG. 15A with a powdered of consumable on the shelf.
Figure 15C:
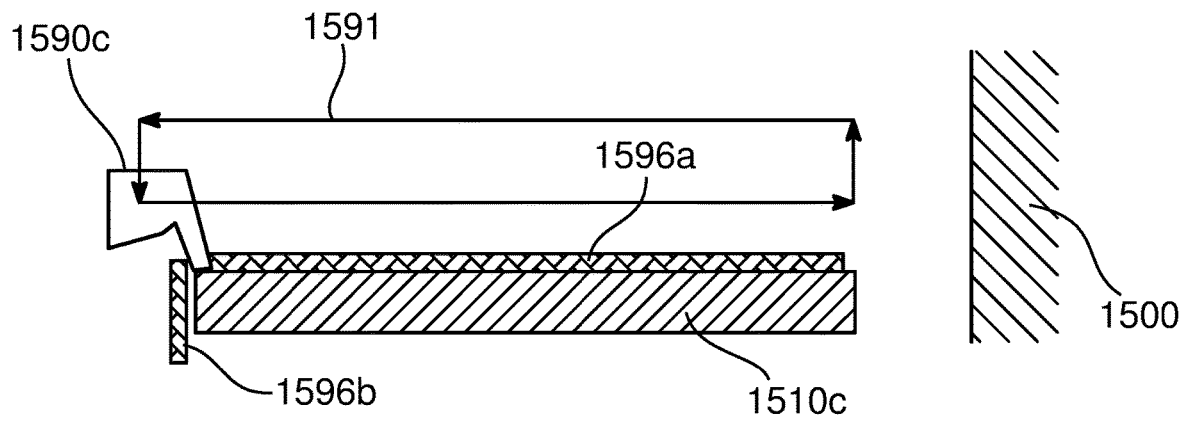
FIG. 15C is a side view of the shelf of FIG. 15A with a solid of consumable on the shelf.

Referring to FIGS. 15A, 15B, and 15C, fecal shelf 1510 is shown with a consumable (1592, 1594, and 1596a) positioned on shelf 1510, and consumable placement mechanism 1590 (a, b, and c). Consumable placement mechanism 1590 follows movement path 1591. As it traverses to the right, consumable placement mechanism 1590 pushes the feces and consumable (1592, 1594, or 1596a) on shelf 1510 off the right side of shelf 1510. Then, consumable mechanism 1590 lifts upward before moving to the left so that it does not disturb the consumable placed on shelf 1510 as it returns to the position shown. FIG. 15a shows consumable 1592, which is a liquid or gel and is positioned by the liquid or gel coming out of consumable nozzle 159a as consumable mechanism 1590a passes from right to left. FIG. 15b shows consumable 1594, which is a powder, and which is positioned by consumable nozzle 159b as consumable mechanism 1590b passes from right to left. FIG. 15C shows consumable 1596a, which increase includes at least a portion which is solid. Consumable 1596A is cut by consumable placement mechanism 1590c on the downward stroke of the mechanism. Consumable 1596b is stored in the toilet and is pulled into position by consumable mechanism 1590c.

Regarding the material choice for the consumable, there are a variety of options and as explained above, the selection of which will depend on many factors. Two important factors are disposability and not compromising other functions of the toilet (such as analysis). One likely candidate for use are biodegradable materials. In one preferred embodiment, this comes in the form of a wood, rice, bamboo, or similar plant-based paper and paper-like products. In another preferred embodiment, this comes in the form of a polymer that breaks down after its intended purpose by bacterial decomposition. An example of a biodegradable hydrophobic coating is a superhydrophobic coating made from cured epoxidized soybean oil and ZnO nanoparticles on cellulosic substrates (see https://pubs.acs.org/doi/abs/10.1021/acssuschemeng.7b02549). An example of a biodegradable hydrophilic material is a cellulose hydrogel produced from okara (see https://www.nature.com/articles/s41598-019-54638-5).

Placement of the consumable may happen at any point before a used deposits feces info the toilet bowl, including during a feces disposal cycle at the end of a previous use of the toilet or just before a user deposits feces into the toilet.

An advantage to placing the consumable at the end of a disposal cycle is that the toilet will immediately be ready for another use. An advantage to placing the consumable just before a use is that the consumable will be freshly applied, which means its effectiveness is less likely to have degraded or compromised for having been placed for too long.

In one preferred embodiment, there is a removal mechanism which removes the feces from the shelf. Additionally, it may remove feces from out of the bowl and into a drain. When used with a consumable to separate the shelf from feces deposited thereon, this mechanism may operate on the consumable and the feces. Alternatively, the mechanism may primarily operate on the consumable and only secondarily on the feces. For example, flush water could act on both the feces and consumable to flush both out of the bowl and into a drain. Alternatively, the removal mechanism may pull the consumable toward a drain. Additionally, as might happen with a hinged shelf, the shelf might angle or drop out from underneath the feces and the consumable acts to reduce the cling of the feces to the bowl so the feces more completely and quickly falls below the shelf.

In one embodiment, the toilet includes a lid which may be closed manually after a user finishes using the toilet. More preferably, the toilet automatically closes the lid when the toilet detects the user is no longer seated, using a proximity or other sensor. The sensor may be in electronic communication with a controller which, in turn, sends a signal to close the lid when the sensor signals that the user has left the toilet. The controller may be connected to the lid through wires, electromagnetic waves (including infrared, visible, and ultraviolet), or other non-wired means. The lid may be in connection with a power source. Additionally, upon receiving the signal from the proximity or other sensor, the controller may initiate other cycles of the toilet, such as excreta processing, excreta analysis, excreta disposal, toilet cleaning and/or sterilizing, hibernation or other low power mode.

In one preferred embodiment, the toilet includes a pump to create a vacuum in the toilet bowl after the lid closes. The vacuum can pull the lid downward toward the toilet seat, applying pressure to the seal or gaskets on the top and/or bottom of the toilet seat. The result is that the toilet becomes a sealed environment within which the toilet may conduct analyses of the user's excreta.

In one preferred embodiment, the toilet includes micro capillary tubes for collecting and/or analyzing samples of excreta.

In one preferred embodiment, the interior of the toilet bowl may house one or more imaging sensors. The image sensors may collect images of the user's feces. In some embodiments, an imaging sensor may collect high resolution images of the feces. In some embodiments, the imaging sensors may collect microscopic images of the feces. The images may be used to assess the user's health status. Additionally, the toilet may be configured to analyze the images. In an example, the images may provide information about the shape, size, density, roughness or texture, and color of the feces. Reflective spectroscopy may also be used to assess texture and color of feces. Laser spectroscopy may also be included to analyze the feces. In one preferred embodiment, the imaging sensor detects optical electromagnetic radiation and/or another portion of the electromagnetic spectrum. Alternatively, the imaging sensors may be related to acoustic or other pressure waves. Alternatively, one or more imaging sensor is outside the bowl and the bowl has at least a portion which is a transparent or translucent medium relative to what is being detected by the imaging sensor, through which the imaging sensor and image the excreta.

In one embodiment, the bowl is made from typical toilet materials like ceramic, plastic, or metal. More preferably, the bowl is made from pressed glass or patterned glass.

In one embodiment, reagents are added to feces while it is on the shelf within the toilet bowl. To facilitate the processing and analysis, the feces may be smeared to a thin layer over a flat surface on the shelf prior to adding the reagents. A device resembling a putty knife or a blade may smear the feces and also mix the feces with the reagents by moving over the fecal sample repeatedly until the reagent and feces are sufficiently mixed. The imaging sensors may collect images of the feces after the reagent has been applied. In some embodiment, the imaging sensor may be housed within the shelf. The shelf may have an optically transparent section above the imaging sensor and the feces may be smeared over this optically transparent area. The imaging sensor may collect images of the thin layer of feces from below the optically transparent area as if it were collecting images of a smear on a glass slide. Alternatively, vibration may be used to reduce excreta to a minimum thickness for analysis.

In a preferred embodiment, the toilet includes a laser which sends a laser beam into the toilet bowl and cuts through the feces. When the cut is made, the fecal material which is internal to the fecal mass may be exposed. The one or more cameras may collect additional images of the interior of the feces. Additionally, VOCs, dioxins, particulate matter, polycyclic aromatic hydrocarbons, carbon monoxide, hexachlorobenzene, and ash may be released from the interior of the feces or created when feces is burnt. A pump may direct the VOCs, vapors, particulates, and other gasses from the process to the sensor where they may be identified and quantified and the data stored on the controller.

Laser beams of a variety of wavelengths may be used to cut through the feces. The density of the feces may be determined by assessing which wavelength best cuts through the feces. The laser beam could be applied to the feces until it is vaporized and may be disposed of in gaseous form. This same technique could vaporize urine for analysis and/or disposal.

Some analysis may have an optimal temperature. In some embodiments, the toilet bowl, other spaces within, or other elements of the toilet may be heated or cooled to conduct analytical reactions on the feces or urine that require specific temperatures. The toilet bowl could also be heated to high temperatures to dehydrate and degrade feces for easier waste processing. High heat could also be used to clean and disinfect the inside of the toilet bowl.

The toilet may include devices housed in the lid which may collect measurements which are relevant to the user's health status. In some embodiments, a device capable of performing photoacoustic imagery may be included in the lid of the toilet. This may be used to map a user's blood oxygenation, detect skin melanoma, and measure methemoglobin. In some embodiments, a device which performs acoustic analysis may be housed within the lid of the toilet. Images of a user's internal organs may be obtained using acoustic analysis while the user is seated on the toilet. In some embodiments, a stethoscope may be housed within the lid of the toilet. The user may lean back against the stethoscope in the lid while seated on the toilet. The stethoscope may be in communication with a controller which may record the sounds of the user's heartbeat and breathing as detected by the stethoscope.

VOC information and other information from user or excreta analysis may be relevant to the user's health status and may be stored on the memory of a controller which may be included within the toilet or located remotely. Camera images may be stored in a memory of the controller which may be included in the toilet or located remotely.

There are many acceptable material choices, methods of manufacture, and methods of assembly for the various parts of the toilet. The selection of materials, manufacturing processes, and assembly depends on a number of factors, including durability, expected forces, expected temperature range, aesthetics, accessibility, potential exposure to corrosive materials, ease of manufacture or assembly, cost, weight, excreta processing and analysis to be performed, ease of cleaning and sterilizing, power requirements, health and wellness assistance provisions to be incorporated, comfort, and other expected user preferences.

In one preferred embodiment, the toilet bowl, lid, valving, and other structures and mechanism are made from plastics. In another preferred embodiment, based on factors as discussed above, plastic materials are selectively exchanged with metals, ceramics, rubber, or even organic materials (such as paper) which are better suited for the application.

Referring to FIGS. 4A, 4B, and 5, in the one preferred embodiment, secondary processing area 520 is accessible by a probe 580 capable of taking a sample of the feces. More preferably, as shown in FIGS. 4A and 4B, this probe is a needle 480 with a hollow to create and hold the sample. In FIG. 4A, needle 482 is in a storage position within toilet 400. In FIG. 4B, needle 482 has extended into secondary processing area 420. After the probe receives the probe can then transfer the sample from the feces to another location for processing and analysis. For example, probe 580 may eject the sample into chamber 590 where it is mixed with water and/or a reagent, following which, sensor 548 may take readings of the mixture. Alternatively, the mixing and/or analyzing may be performed within the probe.

In another alternative embodiment, the probe comprises a mechanism 192 which actuates rotationally or laterally relative to the feces to take a slice of the feces. In another embodiment, the probe comprises an actuator that pushes the feces onto hardware that takes and/or analyses a sample of the feces.

Preferably, the toilet includes a system for sensing and/or controlling the location and orientation of the probe. Controlling the location and/or orientation of the probe may be accomplished in many ways, including the use of structures that selectively or permanently limit the probe's degrees of freedom; the use of motors, especially servomotors; the use of pneumatic or hydraulic systems; and the use of electromagnetic positioning systems. Sensing the location and/or orientation may also be accomplished in many ways, the selection of which is made based on what system—if any—is selected for controlling the location and/or orientation of the probe. Systems that sense the location and/or orientation may include a feedback system built into the motor, an optical sensor, a resistance sensor, a magnetic sensor, and a contact or other type of switch. Alternatively, the toilet may have a system that calculates the location and/or orientation of the probe through such factors as predetermined mechanical limits on the probe's motion and inputs given to the hardware controlling the location and/or orientation.

Location and/or orientation information about the probe may be used to limit or control what functions of the toilet may be allowed. For example, if the system determines that the probe has not returned to its non-use position, this information may be used to prevent the toilet from flushing. Similarly, the toilet may include other means of detecting or calculating its own state, the state of feces within the toilet, and/or the state of urine within the toilet and use these states to control functions of the toilet. In one embodiment, the function of using these states to control the functions of the toilet is especially critical in cleansing the portions of the toilet that receive, process, and/or analyze excreta to prevent contamination of the excreta and help ensure the integrity of the analyses. For example, if the toilet detects the presence of feces on the shelf during what might otherwise be the end of a flush or cleaning phase, the toilet may extend the cleaning phase and take extra steps to clean the shelf, such as applying more water or burning of the feces with high temperature.

There are many ways to analyze the excreta, which can largely be categorized by whether or not the toilet additionally processes it. For example, analysis such as weighing, optical analysis, spectrometry, and durometer testing can be performed in place without moving or dissecting the excreta. For analyses which require the use of consumables (such as adding a reagent to a feces or urine solution), a small portion of the excreta may be taken to lower the amount of consumable and or time required to receive data; this improves the appeal of the toilet as an excrement testing system through improvements such as lowering start-up and operational costs, reducing the time required between uses, extending time between maintenance events (such as refilling consumables), and saving space. As such, other analyses can involve additional processing or manipulating of the excreta, such as dividing or removing a portion of feces or urine from itself, mixing excreta to create a solution, burning or vaporizing excreta, pressing feces, and/or dehydrating excreta. Each analysis that is possible for the toilet to perform includes inherent methods, structures, and equipment that enable the completion of the analysis, creation of data, recording and storing the data, and outputting the data in a usable form. These methods, structures, and equipment, whether preexisting or invented for this toilet, are configured especially for the toilet regardless of any broader or alternative applications. In one embodiment, the toilet is configured with internal digital storage memory where analysis data on one or more feces property may be stored. In one embodiment, the toilet may be configured to export the analysis data to electronic hardware located exterior to the toilet; this data export may be a wired connection, a wireless connection using electromagnetic radiation, or even pressure waves (audible or inaudible). In one embodiment, analysis data may be presented to a person via a display built-in to the toilet. In another embodiment, analysis data may be processed and/or summarized before being presented.

In a preferred embodiment, the feces is deposited into water where it may be mixed and/or dissolved to a relatively homogenous solution. Reagents may then be added to the solution which may indicate the composition of the feces. Examples of reagents include: a biological stain; a colorimetric reagent including Coomassie Brilliant Blue G-250 dye to identify the amount of protein in the solution; Oil red-O to detect lipid in the solution; reagents used in colorimetric assay or those which may result in a product that can be detected using spectroscopy at other wavelengths, such as ultraviolet, infrared, or near infrared; reagents that can produce a fluorescent signal upon interaction with components of the feces, which signal could be detected using a device included in the toilet.

One property that can be determined is the energy with which excreta is deposited in the toilet. If a user is sitting on the toilet seat, this could provide an estimate of the force a user exerted to expel the excreta from their body.

All patents, published patent applications, and other publications referred to herein are incorporated herein by reference. The invention has been described with reference to various specific and preferred embodiments and techniques. Nevertheless, it is understood that many variations and modifications may be made while remaining within the spirit and scope of the invention.

What is claimed is:

1. A toilet comprising:
a bowl adapted to receive feces;
a shelf in the bowl for receiving at least a portion of the feces;
a mechanism that places a consumable material on the shelf between uses of the toilet, so as to separate the feces from the shelf; and
a removal mechanism comprising a water flush for removing the feces and the consumable material from the bowl.

2. The toilet of claim 1, wherein the water flush carries the feces and the consumable material out of the bowl and into a drain.

3. The toilet of claim 1, wherein the consumable material is in the form of a solid sheet.

4. The toilet of claim 3, wherein the sheet comprises paper.

5. The toilet of claim 3, wherein the solid sheet comprises a polymer.

6. The toilet of claim 3, wherein the removal mechanism comprises a device that pulls the solid sheet with the feces on top of it toward a drain.

7. The toilet of claim 3, wherein the mechanism that places the consumable material comprises a continuous roll of the solid sheet from which a portion of the solid sheet is pulled onto the shelf between uses.

8. The toilet of claim 3, wherein the mechanism that places a consumable material comprises a stack of solid sheets, from which an individual sheet from the stack is placed onto the shelf between uses.

9. The toilet of claim 1, wherein the consumable material is in the form of a powder.

10. The toilet of claim 9, wherein the powder comprises talc.

11. The toilet of claim 1, wherein the consumable material comprises a liquid.

12. The toilet of claim 11, wherein the liquid forms a hydrophobic coating on the shelf.

13. The toilet of claim 1, wherein the consumable material is sprayed onto the shelf prior to feces being deposited thereon.

14. The toilet of claim 1, wherein the consumable material is spread onto the shelf by a mechanical spreader prior to feces being deposited thereon.

15. The toilet of claim 1, wherein the consumable material is manually put in place.

16. The toilet of claim 1, wherein the consumable material is automatically put in place.

17. The toilet of claim 1, further comprising a supply of the consumable material stored in the toilet prior to being positioned on the shelf.

18. The toilet of claim 17, further comprising a sensor that detects a property of the supply of the consumable material useful in determining when the supply is insufficient to be placed on the shelf.

19. The toilet of claim 1, wherein the removal mechanism comprises at least one of the group containing a squeegee that wipes feces from the shelf, a mechanism that pushes the feces, a mechanism attached to the shelf which vibrates the shelf, a piezoelectric device, pressure waves bombarding the feces, and a top of the shelf with a permanent non-horizontal angle.

20. The toilet of claim 1, wherein the removal mechanism comprises a mechanism to change the angling of the shelf from an initial horizontal or near horizontal orientation.

* * * * *